(12) United States Patent
Vargas et al.

(10) Patent No.: US 8,425,577 B2
(45) Date of Patent: Apr. 23, 2013

(54) LED PHOTOTHERAPY APPARATUS

(76) Inventors: Joanna Vargas, Edgewater, NJ (US); Cesar Vargas, Edgewater, NJ (US)

( * ) Notice: Subject to any disclaimer, the term of this patent is extended or adjusted under 35 U.S.C. 154(b) by 0 days.

(21) Appl. No.: 13/324,045

(22) Filed: Dec. 13, 2011

(65) Prior Publication Data

US 2012/0150265 A1    Jun. 14, 2012

Related U.S. Application Data

(60) Provisional application No. 61/422,735, filed on Dec. 14, 2010.

(51) Int. Cl.
*A61N 5/06*    (2006.01)
(52) U.S. Cl.
USPC .............. 607/91; 607/88; 607/89; 606/9
(58) Field of Classification Search .............. 607/88–91; 606/9
See application file for complete search history.

(56) References Cited

U.S. PATENT DOCUMENTS

| | | | |
|---|---|---|---|
| 5,766,233 A * | 6/1998 | Thiberg | 607/88 |
| 6,896,693 B2 | 5/2005 | Sullivan | |
| 2002/0198575 A1* | 12/2002 | Sullivan | 607/88 |
| 2006/0030908 A1 | 2/2006 | Powell et al. | |
| 2006/0089687 A1 | 4/2006 | Spooner et al. | |
| 2007/0239143 A1 | 10/2007 | Altshuler | |
| 2007/0276455 A1* | 11/2007 | Fiset | 607/91 |
| 2009/0005839 A1* | 1/2009 | Griffith et al. | 607/91 |
| 2009/0177190 A1 | 7/2009 | Lee | |
| 2009/0222070 A1* | 9/2009 | Daffer | 607/91 |
| 2009/0254156 A1 | 10/2009 | Powell et al. | |

FOREIGN PATENT DOCUMENTS

| | | |
|---|---|---|
| EP | 1839704 A1 | 10/2007 |
| EP | 2001878466 | 1/2008 |
| EP | 2002145649 | 1/2010 |
| JP | 29095416 A | 5/2009 |
| WO | WO 2005065777 A1 | 7/2005 |
| WO | WO 2006/020602 A1 | 2/2006 |
| WO | WO 2007/125336 A1 | 11/2007 |
| WO | WO 2009/137612 A2 | 11/2009 |
| WO | WO 2010/070277 | 6/2010 |

OTHER PUBLICATIONS

PCT International Search Report and Written Opinion; PCT/2011/064648: Vargas, Joanna.

* cited by examiner

*Primary Examiner* — Bill Thomson
*Assistant Examiner* — Jeffrey Lipitz
(74) *Attorney, Agent, or Firm* — Gearhart Law, LLC

(57) ABSTRACT

A red and near infra-red light phototherapy apparatus designed to accommodate an adult user. A user support of the device may have a hingably connected canopy that contains the red, and infra-red, light source. When the canopy is open, a user may lie on the user support. When adjusted to an operational position, the upper light source may illuminate the entire user support. The apparatus may include an acrylic support with a lower red, and infra-red, light source attached beneath. The acrylic support may be transparent to the red, and infra-red, light. The lower light source may illuminate the entire acrylic support from below. The red narrow band, light emitting diodes (LEDs) may be selected to have a wavelength in a range of approximately 625 nm to 645 nm, and the infra-red LEDs to emit in a range of approximately 820 nm to 860 nm.

13 Claims, 5 Drawing Sheets

LED PHOTOTHERAPY APPARATUS

CLAIM OF PRIORITY

This application claims the priority of U.S. Ser. No. 61/422,735 filed on Dec. 14, 2010, the contents of which are fully incorporated herein by reference.

FIELD OF THE INVENTION

The invention relates to a skin treatment device, and more particularly, to an apparatus for the application of red and near infra-red LED phototherapy over large areas of a user's body.

BACKGROUND OF THE INVENTION

With the development of super-luminescent, narrow bandwidth Light Emitting Diodes (LEDs) of the appropriate wavelength, red and near infra-red phototherapy has become a standard non-ablative skin rejuvenation procedure at many aesthetic and dermatological clinics throughout the world.

Non-ablative skin rejuvenation with red LED phototherapy is thought to occur by invoking the body's inflammation response near to the skin surface without damaging the skin. Red light that is substantially 633 nm in wavelength has apparently been shown to make mast cells in the dermis, adjacent to blood vessels, degranulate. This is interpreted by the surrounding tissue as inflammation, causing the body's natural wound healing process to be trigged, even though no actual damage has being incurred. This natural wound healing process then rejuvenates the surrounding tissue.

Additionally, near infrared light, which can penetrate further into tissue than red light, is thought to increase the cells ability to generate ATP. ATP is the chemical that provides power to the cell, so its increased production stimulates the cell's metabolism, further enhancing the beneficial effect of the body's natural healing process triggered by the red light.

To utilize these effects, special lamps have been designed, having both red light and infra-red light LED's of the appropriate intensities and wavelengths for optimal rejuvenation. These lamps, however, are only able to illuminate a small area of the body. It is highly desirable to be able to apply red, and near infra-red, light phototherapy simultaneously over a large area of the body in a safe and controlled manner.

DESCRIPTION OF THE RELATED ART

Relevant art involving phototherapy devices includes:

U.S. Pat. No. 6,896,693 issued to Sullivan on May 24, 2005 for a "Photo-therapy device" that describes a device that is therapeutically beneficial to the well-being of living organisms such as humans, animals, and/or plant life, using photon or light waves. The device is intended to lie against the skin or surface, near the skin/surface, and/or from a distance ranging up to several feet from the skin/surface. The device is intended to be used for: general relaxation and detoxification of an organism; stimulating the healing process in an organism which is ill, diseased or injured; aiding in the elimination of pain and inflammation in an organism; stimulating/sedating the acupressure meridian system of an organism and rebalancing the electromagnetic energy-field surrounding the organism.

US Patent Application no. 20090177190 issued to Lee; Seung Yoon on Jul. 9, 2009 for "Lowering skin melanin appearance with red light radiation and red light radiation kit therefore" that describes a method of reducing appearance of melanin on the skin of a subject comprises exposing the skin to red narrow-band radiation at a wavelength(s) in a range of between 620 nm and 750 nm and having a band width of between 0 nm and 20 nm, in an effective dose to cause the appearance of the skin melanin to diminish and essentially not to cause photothermolysis of the skin. Alternatively, a method of reducing appearance of melanin on the skin of a subject comprises exposing the skin to non-coherent red narrow-band radiation at a wavelength(s) in a range of between 620 nm and 750 nm and having a band width of between 0.1 nm and 20 nm, in an effective dose to cause the appearance of the skin melanin. A portable kit for such a method comprises a radiation source generating red narrow-band radiation at a wavelength(s) in a range of between 620 nm and 750 nm, the narrow band radiation having a band width of between 0 nm and 20 nm and having a power density of between 10 mW/cm.sup.2 and 120 mW/cm.sup.2, and a manual instructing a user how to use the red narrow-band radiation for red narrow-band irradiation treatment to reduce appearance of melanin on the skin of a subject.

US Patent publication 20040068305 submitted by Bansal et al. on Apr. 8, 2004 entitled "Phototherapy system and device" that discloses a phototherapy system and device including an array of light sources arranged so as to achieve substantially uniform distribution of light on a subject. The light sources can be arranged in a number of configurations, including but not limited to distributions in which the density of lights sources is greater in the periphery than in the center. The present invention also includes a light diffusing panel to increase exposure uniformity, and a targeting mechanism to ensure that the device is properly aligned over the subject.

Various, related implements are known in the art, but fail to address all of the problems solved by the invention described herein. One embodiment of this invention is illustrated in the accompanying drawings and will be described in more detail herein below.

SUMMARY OF THE INVENTION

The present invention relates to a combined red and near infra-red light phototherapy apparatus. In a preferred embodiment, the red, and near infra-red, light phototherapy apparatus may have red and near infrared light sources that are, for instance, made up of a number of light emitting diodes (LEDs), some of which emit light in a narrow band of red wavelengths and some in a narrow band of infra-red wavelengths. LEDs of both wavelengths may, for instance, be included in both an upper red and infra-red light source and a lower red and infra-red light source of the device.

The red and near infra-red light, phototherapy apparatus may, for instance, also include a user support that is preferably designed to accommodate an adult user in either a prone, or a supine, orientation, i.e., lying down either on their back or stomach. The user support may have a canopy attached to it that may contain the upper red and infra-red light source, and may be hingably connected to the user support. When the canopy is open, a user may have easy access to the user support, and when it is adjusted to an operational position, the upper red and infra-red light source may then be positioned to provide red and infra-red light illumination to substantially the entirety of the user support, from above the support.

The user support of the red and near infra-red light, phototherapy apparatus may also include an acrylic support portion with a lower red and infra-red light source attached beneath the acrylic support portion. The acrylic support portion is preferably substantially transparent to the range of wavelengths emitted by the red and infra-red light. The lower red and infra-red light source may be positioned to provide red and infra-red light illumination to substantially the entirety of the acrylic support portion from below the support.

In a highly preferred embodiment, the red narrow band, light emitting diodes (LEDs) may be selected to provide light having a wavelength in a range of approximately 625 nm to 645 nm and the infra-red LEDs may be selected to provide light having a wavelength in a range of approximately 820 nm to 860 nm.

Therefore, the present invention succeeds in conferring the following, and others not mentioned, desirable and useful benefits and objectives.

It is an object of the present invention to provide a phototherapy system that is compatible with existing skin rejuvenation techniques.

It is another object of the present invention to provide an apparatus that stimulates the bodies own cellular mechanisms by photo-modulation.

Yet another object of the present invention is to provide a non-invasive, non-ablative safe therapy.

Still another object of the present invention is to do no damage to sub-dermal tissue.

Still another object of the present invention is to provide an apparatus that allows treatment of large areas, including the entire body.

Yet another object of the present invention is to provide a system that is compatible with cosmetic surgery such as blepharoplasty and breast reduction and augmentation.

Still another object of the present invention is to provide an apparatus that is easy to operate and very cost-effective.

DESCRIPTION OF THE PREFERRED EMBODIMENTS

Figure 1:
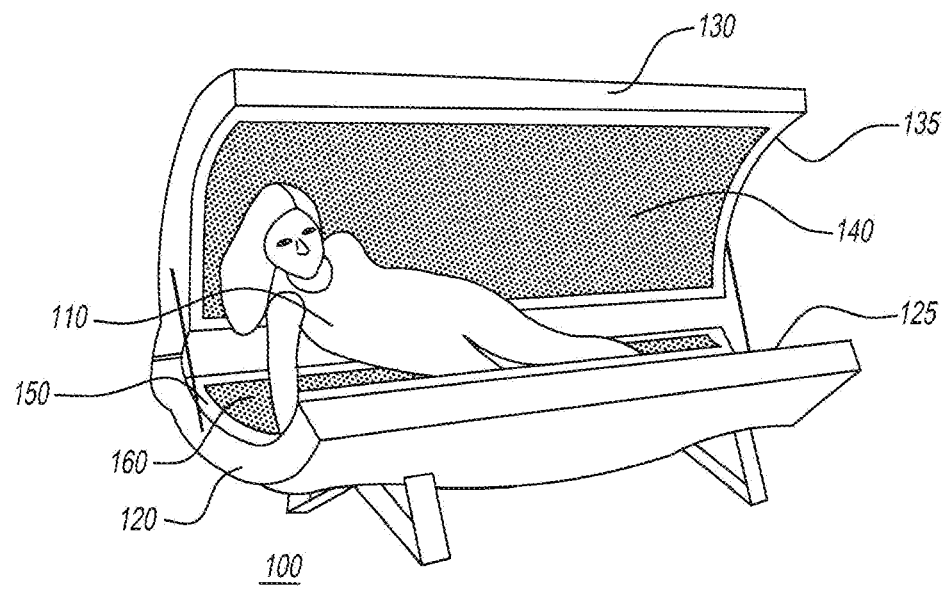
FIG. 1 shows a perspective view of the red and near infra-red light, phototherapy apparatus of the present invention with the canopy in an open position.

The preferred embodiments of the present invention will now be described with reference to the drawings. Identical elements in the various figures are identified with the same reference numerals.

Reference will now be made in detail to an embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

FIG. 1 shows a perspective view of the red, and near infra-red, light phototherapy apparatus 100 of the present invention with the canopy in an open position. In this figure, a user 110 is shown reclining on the user support 120 with the canopy 130 in an open position to allow the user 110 to appropriately situate themselves on the red, and near infra-red, light phototherapy apparatus 100. The user 110 may, for instance, assume a variety of positions for therapy, though a prone position, i.e., lying on their back, or a supine position, i.e., lying on their stomach, are the most common positions selected by users.

When the canopy 130 is open, both the upper red and infra-red light source 140 and the lower red and infra-red light source 160 are typically turned off.

The upper red and infra-red light source 140 may, for instance, be attached to the canopy 130 that is hingibly connected to the user support 120. When the canopy 130 is adjusted to an operational position, the upper red and infra-red light source 140 may be located so as to provide red and infra-red light illumination to substantially the entirety of the user support 120 from above the user 110.

The lower red and infra-red light source 160 may be positioned beneath the user 110, typically under an acrylic support portion 150 that may form part of the user support 120. The lower red and infra-red light source 160 may be positioned to provide red and infra-red light illumination to substantially the entirety of the acrylic support portion 150 from below the user 110.

In a preferred embodiment, the red and infra-red light illumination provided by the upper red and infra-red light source 140 and the lower red and infra-red light source 160 may be substantially uniform over the entirety of the user surface 125 of the user support 120.

Figure 2:
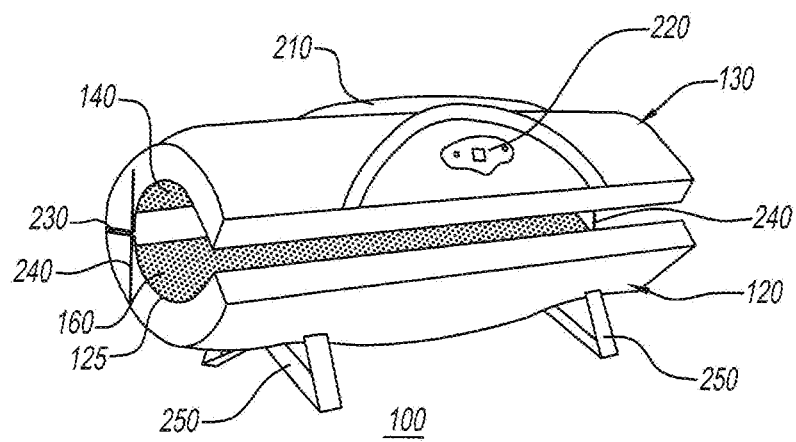
FIG. 2 shows a perspective view of the red-light, phototherapy apparatus of the present invention with the canopy in a closed position.

FIG. 2 shows a perspective view of the red and near infra-red light, phototherapy apparatus 100 of the present invention with the canopy in a closed position.

With the canopy 130 closed, a user 110 (not shown in this view) residing on the user surface 125 may be illuminated by both the upper red and infra-red light source 140 and the lower red and infra-red light source 160 that may both now be turned on. The red and infra-red light sources may, for instance, be made operative by means of a power-source 210 that may be controlled by a control panel 220. Both the power-source 210 and the control panel 220 may, for instance, be incorporated into the canopy 130.

The hinged canopy 130 may be closed with the assistance of the hinge 230 and the expandable struts 240 that may be hydraulically damped or otherwise spring loaded to make opening or closing the canopy 130 easier. One of ordinary skill in the art will readily appreciate that many hydraulic, mechanical and electrical arrangements may be used to open or close, or assist in opening or closing, the canopy 130.

In the closed, operational position, the upper red and infra-red light source 140 may be located to provide red and infra-red light illumination to substantially the entirety of the user surface 125 from above the user.

The user surface 125 may include an acrylic support portion 150 that is substantially transparent to the range of wavelengths emitted by the red and infra-red light LEDS so that in the closed, operational position, the lower red and infra-red light source 160 may be positioned to provide red, and infra-red, light illumination to substantially the entirety of the user surface 125 from below the user.

In a preferred embodiment, the phototheraphy device may be sized to accommodate an adult user of either sex. One of ordinary skill in the art will readily appreciate that the size and shape of the device may be adapted to preferential for either children or for one or other sex or some combination thereof, by for instance, arrangement of the lights or by the contouring of the support acrylic.

Also shown in FIG. 2 are ground supports 250 that may be used to maintain the red and near infra-red light, phototherapy apparatus 100 in a stable, stationary position. One of ordinary skill in the art will readily appreciate that the ground supports 250 may, for instance, include lockable wheels to allow easy repositioning of the red and near infra-red light, phototherapy apparatus 100.

Figure 3:
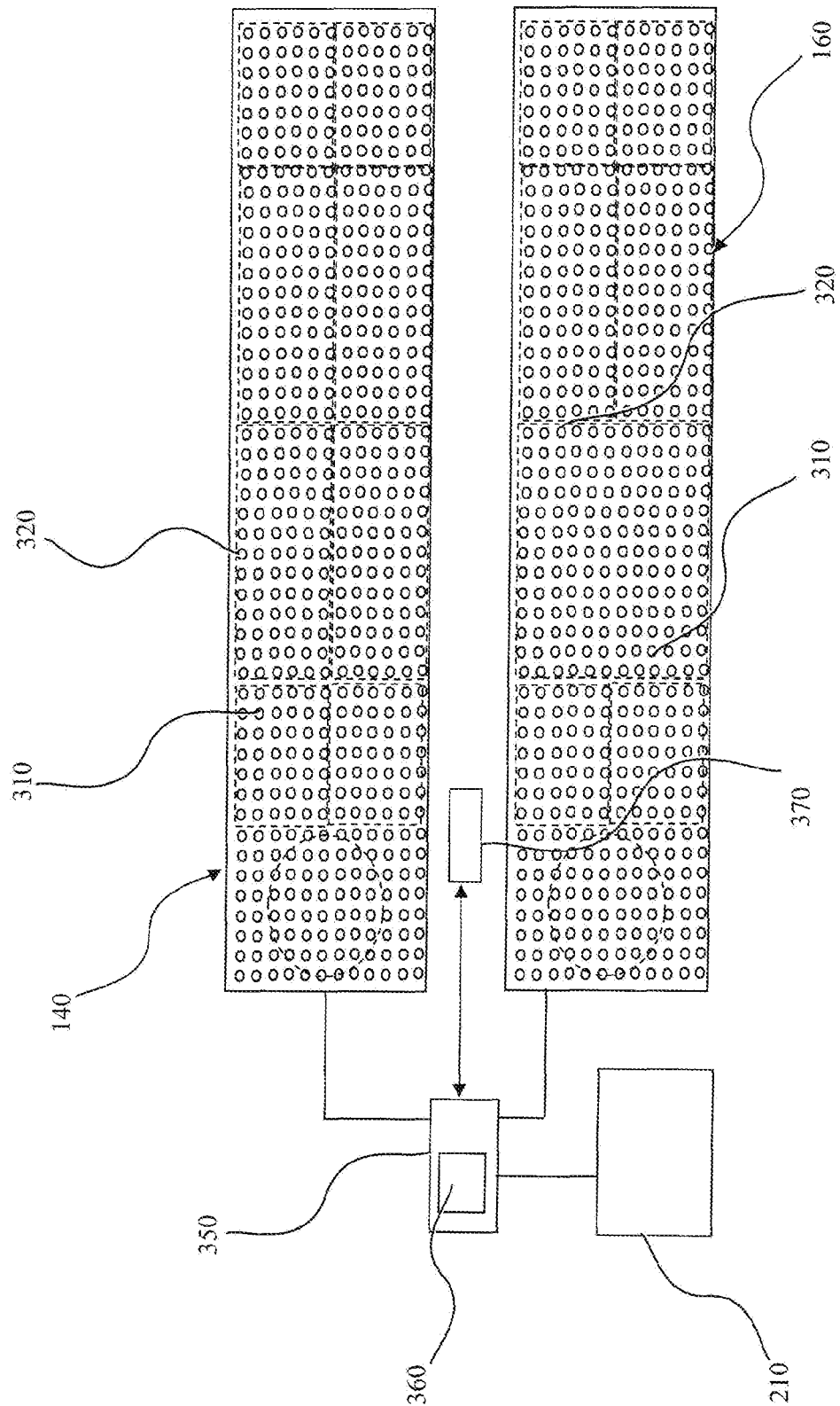
FIG. 3 shows a schematic view of the control and illumination systems of the red and near infra-red light, phototherapy apparatus of the present invention.

FIG. 3 shows a schematic view of the control and illumination systems of the red and near infra-red light, phototherapy apparatus of the present invention.

As shown schematically in FIG. 3, the upper red and infra-red light source 140 may consist of a plurality of narrow band, light emitting diodes (LEDs) 310.

The LEDs may be supplied with power by the power-source 210 under the control of the exposure control unit 350 that may have a suitable user interface 360. The exposure control unit 350 may further be controlled by a wireless user interface 370 that may be operated by the user 110 while undergoing therapy, or by the therapist overseeing the therapy, or some combination thereof. The power-source 210 may be a suitable source of electricity such as, but not limited to, an electrical battery or an electrical mains connection, or some combination thereof. The exposure control unit 350 may, for instance, include a suitably programmed general purpose computer.

The LEDs may have an adjustable exposure intensity that may, for instance, be accomplished by means of a variable mark/space ratio of the LED's, i.e., they may each have on/off cycles on the order of milliseconds, and the percentage time that the light is on to the time it is off, may be varied.

The plurality of narrow band, light emitting diodes (LEDs) 310 may, for instance, be arranged in a multiplicity of illumination regions 320. Each of the illumination regions 320 may be a collection of LEDs whose illumination time or intensity may be cooperatively controlled by the exposure control unit 350. For instance, each exposure region may be set to an exposure intensity that is different from the other regions, either by varying the current supplied to the LEDs in that region, or by varying the mark/space ratio of the illumination within that region, or some combination thereof. In this way, different parts of the user's 110 body may be subject to a different degree of therapy. The multiplicity of illumination regions 320 may be any useful shape such as, but not limited to, a square, a rectangle, an oval, a circle, a triangle or some combination thereof.

In an alternate embodiment, the red and near infra-red light, phototherapy apparatus 100 may include a substantially transparent acrylic 135 disposed between the user and the upper red and infra-red light source 140. The substantially transparent acrylic 135 may have a substantially uniform transmission to the wavelengths of the upper red and infra-red light source 140 or it may have regions of different transmission to the wavelengths, including the peak wavelengths, of the upper red, and infra-red, light sources.

The regions of different transmission may, for instance, be the result of either a difference in thickness, a difference in composition, a presence of an absorbing film, or some combination thereof.

The substantially transparent acrylic 135 may also, or instead, be made of materials or have shaped structures, or some combination thereof, that diffuses the radiation transmitted through substantially transparent acrylic 135.

Figure 4:
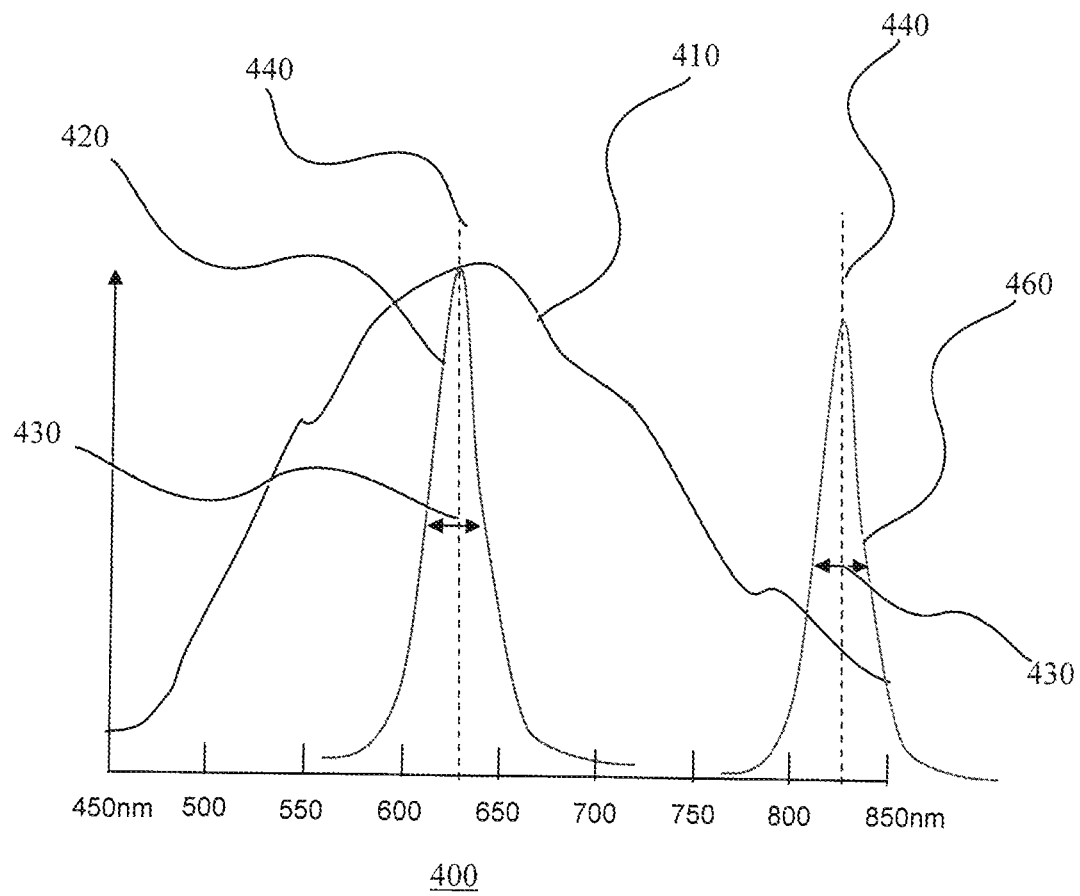
FIG. 4 shows a spectrum of the light emission of two exemplary LEDs used in the red, and near infra-red, light phototherapy apparatus of the present invention.

FIG. 4 shows a graph comparing a spectrum of the light emission of two exemplary LEDs used in the red and near infra-red light, phototherapy apparatus 100 of the present invention to a visible light spectrum emitted by an incandescent bulb.

As shown in FIG. 4, the visible light spectrum emitted by an incandescent bulb 410 extends from beyond 450 nm, i.e., the blue end of the spectrum, to beyond 850 nm, i.e., the infra-red end of the spectrum. In contrast, the visible light spectrum emitted by the ultra-bright, narrow band red LED 420 has a mid spectrum wavelength 440 of about 630 nm, i.e., red, and rapidly falls away in intensity on either side to a full width, half maximum (FWHM) wavelength range 430 that extends from about 620 nm to about 660 nm, all still in the red portion of the spectrum.

It is this narrow bandwidth of the LED in the red portion of spectrum that allows the body's inflammation response to be activated in cells near to the skin surface without damaging the skin, thereby enabling non-ablative skin rejuvenation phototherapy to occur, i.e., the body's natural wound healing process may be trigged even though no actual damage has been being incurred.

The light spectrum emitted by an ultra-bright, narrow band infra-red LED 460 has a mid spectrum wavelength 440 of about 830 nm, i.e., infra-red, and rapidly falls away in intensity on either side to a full width, half maximum (FWHM) wavelength range 430 that extends from about 815 nm to about 850 nm, all still in the infra-red portion of the spectrum.

It is this narrow bandwidth of the LED in the ultra-red portion of spectrum that allows the cells to increase ATP production and, thereby, their metabolism, and so aid the rejuvenation process.

Manufacturers such as, but not limited to, Roithner Lasertechnik of Vienna, Austria and OSRAM Opto Semiconductors Inc of Regenberg, Germany, supply suitable LEDs such as, but not limited to, an ultrabright red light emitting diode (LED) with a peak output at 633 nm and full width at half maximum (FWHM) of 16 nm or a peak output at 25 nm with a FWHM about 15 nm.

To use the red and near infra-red light, phototherapy apparatus 100, an appropriately clothed, semi-clothed or unclothed, user 110 may lie down on the user support 120 while the canopy 130 is in the open position. The user 110, or an assistant, may then lower the canopy 130 by, for instance, activating the expandable struts 240 using the wireless user interface 370, or by simply lowering the canopy down by hand.

Once the canopy is lowered, the upper red and infra-red light source 140 and the lower red and infra-red light source 160 may be activated by, for instance, the user with the wireless user interface 370 or an assistant using the suitable user interface 360. The user may be exposed to a preselected intensity of red-light, and infra-red light, for a preselected time, or the intensity of the illumination may vary according to a predetermined schedule to provide therapy appropriate for the user. The illumination may also be varied in time, or intensity, by wavelength or by geometry using the multiplicity of illumination regions 320, or some combination thereof. In this way, appropriate, but different therapy regimes may be applied to different parts of the user's body.

When a user has finished using the red-light, phototherapy apparatus 100, it may then be cleaned, or otherwise sanitized, so as to be ready for a next user.

Figure 5:
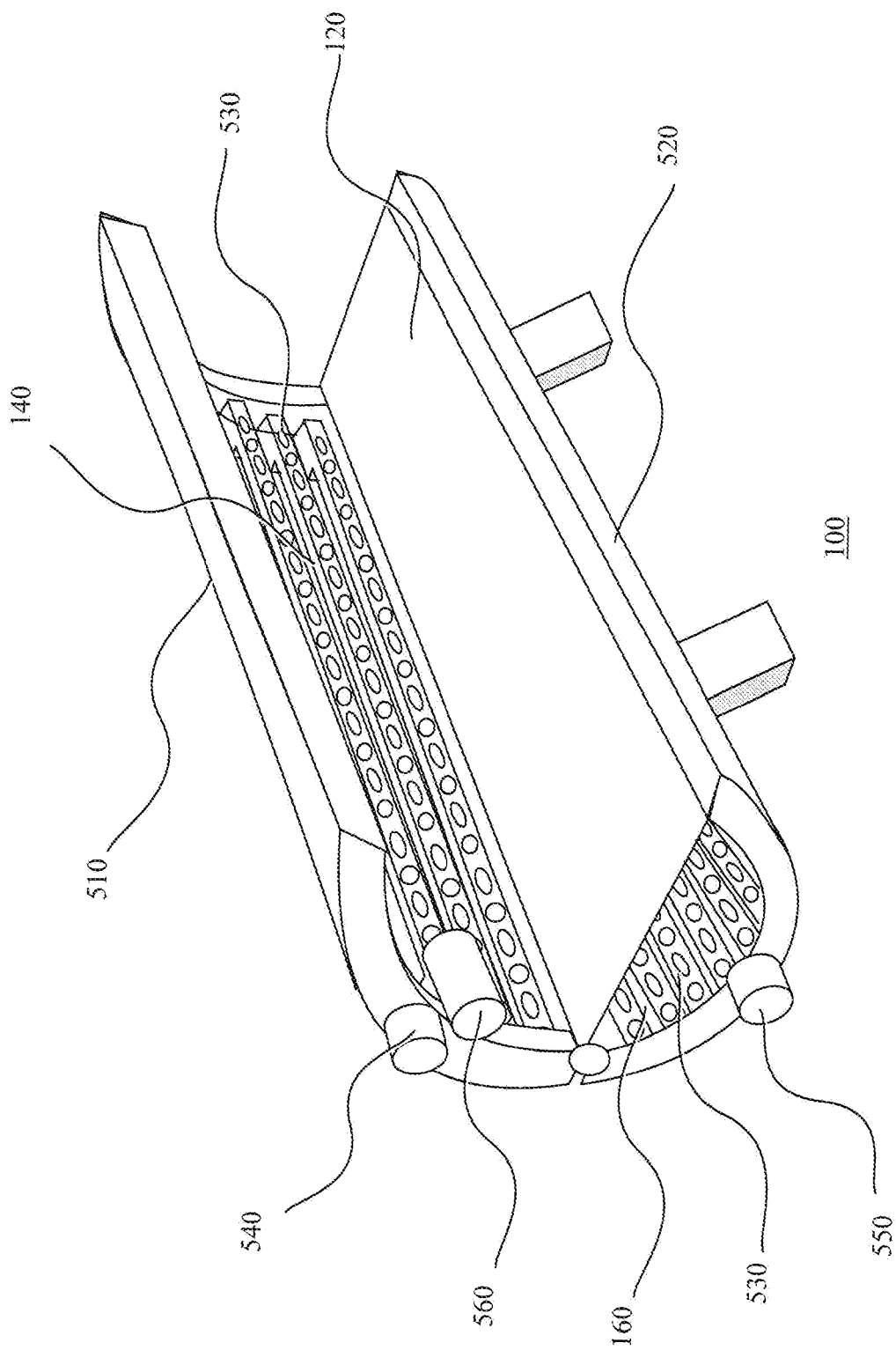
FIG. 5 shows a perspective view of a further embodiment of a red, and near infra-red, light phototherapy apparatus of the present invention.

FIG. 5 shows a perspective view of a further embodiment of a red and near infra-red light, phototherapy apparatus of the present invention.

The red and near infra-red light, phototherapy apparatus 100 is shown with the upper clam 510 in an open position to display the upper red and infra-red light source 140. In this embodiment, the upper red and infra-red light source 140 may be made up of at least one multi-bulb LED strip 530 in which a plurality of LEDs are attached to a base and may all be installed as a single unit.

The lower red and infra-red light source 160, shown beneath the user surface 125, may also be made up of at least one multi-bulb LED strip 530.

The red and near infra-red light, phototherapy apparatus 100 of this embodiment may also include a upper clam cooling fan 540, a lower clam cooling fan 550 and a user cooling fan 560.

The upper clam cooling fan 540 may cool the upper red and infra-red light source 140 or maintain it at a fixed temperature. The upper clam cooling fan 540 may operate automatically whenever the upper red and infra-red light source 140 is turned on, or it may be controlled wholly or in part, by a thermostat arrangement. The thermostat arrangement may, for instance, include a suitable temperature measuring probe that may send data pertaining to the temperature of the upper red and infra-red light source 140 to the exposure control unit 350. The exposure control unit 350 may, for instance, include suitably programmed general purpose electronic computing hardware that may also control the operation of the upper clam cooling fan 540.

The lower clam cooling fan 550 may operate in a similar fashion with respect to the lower red and infra-red light source 160.

The lower clam cooling fan 550 (on the lower clam 520) may operate to cool the region between the upper red and infra-red light source 140 and the user surface 125, or to keep the region, and the user occupying it, at a selected temperature. Operation of the lower clam cooling fan 550 may, for instance, be controlled by the exposure control unit 350 and a suitable temperature monitor in the region between the upper red and infra-red light source 140 and the user surface 125. The lower clam cooling fan 550 may also be controlled via the wireless user interface 370 (shown in FIG. 3), either by a user of the red and near infra-red light, phototherapy apparatus 100, an assistant, or by a professional overseeing the treatment, or some combination thereof.

Figure 6:
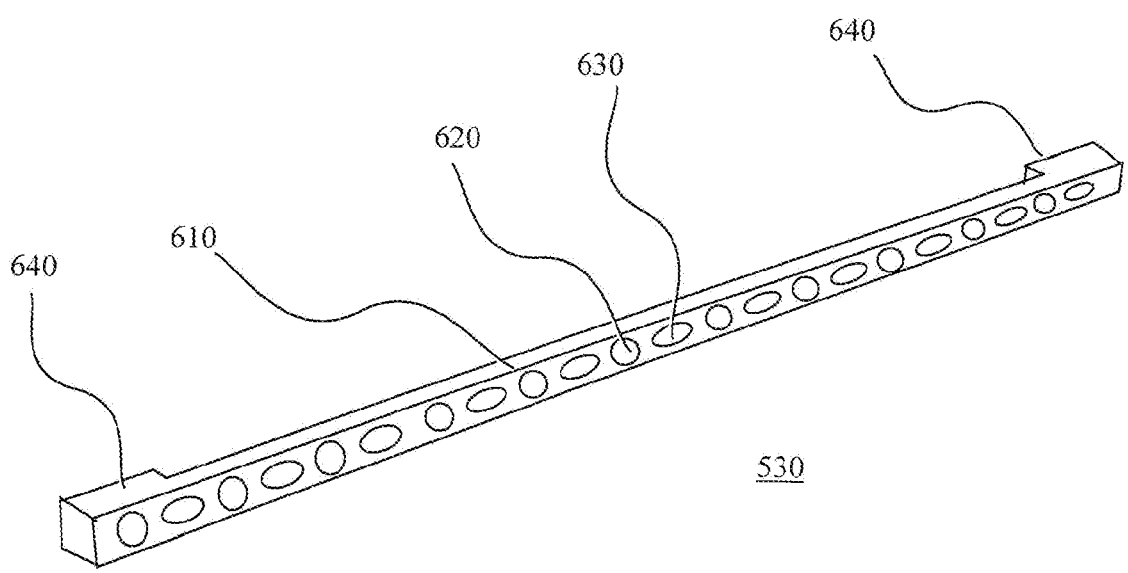
FIG. 6 shows a perspective view of multi-bulb LED strip of the present invention.

FIG. 6 shows a perspective view of multi-bulb LED strip of the present invention.

The multi-bulb LED strip 530 may have both red light LEDs 620 and near infrared LEDs 630 mounted on a multi-bulb LED strip base 610. The multi-bulb LED strip base 610 may be any suitable holder such as, but not limited to, a plastic strip, a metal strip, an aluminum strip or some combination thereof. The LEDs may attached to, or mounted on, the multi-bulb LED strip base 610 by any suitable means such as, but not limited to, gluing, soldering, riveting, a plastic or metal spring clip.

The multi-bulb LED strip 530 may also include a multi-bulb LED strip plug 640 so that all the LEDs on the multi-bulb LED strip 530 may be wired to a single contact point. In this way the multi-bulb LED strip 530 may be installed and removed in a manner similar to a long fluorescent tube. The LEDs may be arranged in any manner, but in a preferred embodiment, they alternate between a red light LED 620 and a near infrared LED 630 and are arranged linearly and evenly spaced along the multi-bulb LED strip base 610. The multi-bulb LED strip 530 may be of any suitable length thought in a preferred embodiment the multi-bulb LED strip 530 is substantially equal in length to the red and near infra-red light, phototherapy apparatus 100 or to the user surface 125 of the user support 120.

In a further embodiment, the multi-bulb LED strip base 610 may be made of a suitably rigid transparent material such as, but not limited to, acrylic plastic, glass, non-acrylic patristic or some combination thereof. In such an embodiment the LEDs may be mounted so that the light is emitted through the transparent multi-bulb LED strip base 610 that may also act as a protection shield.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed:

1. A red and near infra-red light, phototherapy apparatus, comprising:
a user support having a user surface comprising an acrylic support portion and a lower red-light source attached beneath said acrylic support portion, said acrylic support portion being substantially transparent to a range of wavelengths emitted by a red-light Light Emitting Diode (LED) source and by and infra-red light LED source; and wherein said light sources are positioned to provide red-light and infra-red light illumination to substantially the entirety of said acrylic support portion from below;
a canopy;
an upper red and infra-red light LED source attached to said canopy such that, when said canopy is adjusted to an operational position, said upper red and infra-red light LED sources are located to provide red and infrared light illumination to substantially the entirety of said user surface of the user support, from above; and
wherein said upper and lower red and infra-red light LED sources comprise at least one removable multi-bulb LED strip, said removable multi-bulb LED strip having a rigid base substantially equal in length to the support and being comprised of evenly spaced alternating red and infra-red LED light sources; and
wherein said red-light LED source provides light substantially exclusively in a narrow bandwidth, wavelength range of approximately 625 nm to 645 nm, and said infra-red light LED source provides light substantially exclusively in a narrow bandwidth, wavelength range of approximately 820 nm to 860 nm.

2. The apparatus of claim 1 further including a power-source operatively connected to said upper red and infra-red light source; and where said canopy is hingably connected to said user support.

3. The apparatus of claim 1 wherein said user support provides support to either a prone or a supine adult user.

4. The apparatus of claim 1 wherein said red-light and said infra-red light illumination is substantially uniform over the entirety of said user surface of said user support.

5. The apparatus of claim 1 wherein both said upper and lower red and infra-red light sources may comprise a multiplicity of illumination regions and wherein each of said exposure regions may be set to an adjustable exposure time or intensity.

6. The apparatus of claim 5 where said adjustable exposure time or intensity may be a variable mark/space ratio of each of a plurality of narrow band, light emitting diodes.

7. The apparatus of claim 6 further comprising an exposure control unit having a suitable user interface.

8. The apparatus of claim 7 further comprising a wireless user interface.

9. The apparatus of claim 1 further comprising a substantially transparent acrylic disposed between a user and said upper red and infra-red light source.

10. The apparatus of claim 9 wherein said substantially transparent acrylic has regions of different transmission to a peak wavelength of said upper red light source or said upper infra-red light source.

11. The apparatus of claim 10 where the different transmission is a result of either a difference in thickness, a difference in composition, a presence of an absorbing film or some combination thereof.

12. The apparatus of claim 9 where said substantially transparent acrylic further comprises materials or shaped structures, or some combination thereof, that diffuses radiation transmitted through said substantially transparent acrylic.

13. The apparatus of claim 1 further including one of a upper clam cooling fan, a lower clam cooling fan and a user cooling fan or some combination thereof.

* * * * *